(12) United States Patent
Lockery

(10) Patent No.: US 11,654,434 B2
(45) Date of Patent: May 23, 2023

(54) MICROINJECTION CHIP, DEVICE, SYSTEM AND USES THEREOF FOR UNICELLULAR OR MULTICELLULAR ORGANISMS

(71) Applicants: NemaMetrix Inc., Eugene, OR (US); University of Oregon, Eugene, OR (US)

(72) Inventor: Shawn Lockery, Eugene, OR (US)

(73) Assignees: NemaMetrix Inc., Eugene, OR (US); University of Oregon, Eugene, OR (US)

( * ) Notice: Subject to any disclaimer, the term of this patent is extended or adjusted under 35 U.S.C. 154(b) by 127 days.

(21) Appl. No.: 16/449,707

(22) Filed: Jun. 24, 2019

(65) Prior Publication Data

US 2019/0388892 A1    Dec. 26, 2019

Related U.S. Application Data

(60) Provisional application No. 62/689,245, filed on Jun. 24, 2018.

(51) Int. Cl.
  *B01L 3/00* (2006.01)
  *C12M 1/26* (2006.01)
  (Continued)

(52) U.S. Cl.
  CPC .... *B01L 3/502761* (2013.01); *A01K 67/0336* (2013.01); *B01L 3/50273* (2013.01);
  (Continued)

(58) Field of Classification Search
  CPC ........ B01L 3/502761; B01L 3/502715; B01L 3/502753; B01L 3/50273;
  (Continued)

(56) References Cited

U.S. PATENT DOCUMENTS 6,645,432 B1    11/2003   Anderson et al.
2006/0215155 A1*  9/2006   Weber ..................... B29C 65/58
                                                  356/246
(Continued)

FOREIGN PATENT DOCUMENTS

WO          0188087 A2    11/2001
WO    WO-2016063199 A1 *  4/2016  ............ B01L 3/5085

OTHER PUBLICATIONS

Ayamura et al., "Local guiding of C. elegans inside micro-channel for injection operation", 2015, IEEE/SICE International Symposium on System Integration (Year: 2015).*

(Continued)

*Primary Examiner* — Jill A Warden
*Assistant Examiner* — Henry H Nguyen
(74) *Attorney, Agent, or Firm* — Koren Anderson

(57) ABSTRACT

Disclosed herein are microinjection chips, devices, and systems for injection of unicellular or multicellular organisms. The microinjection chip and device disclosed herein include the microfluidic features, inlet port, pre-injection reservoir, injection channel and post injection channel in fluid communication with each other. The inlet port is adapted to sequentially move individual organisms into the injection channel, which is adapted to immobilize the individual organism in fluid. The injection channel features a side wall adapted to receive a microinjection pipette without a microinjection port and to reseal when the microinjection pipette is removed.

16 Claims, 7 Drawing Sheets

(51) Int. Cl.
*A01K 67/033* (2006.01)
*C12N 15/89* (2006.01)

(52) U.S. Cl.
CPC ... *B01L 3/502715* (2013.01); *B01L 3/502753* (2013.01); *C12M 33/04* (2013.01); *C12N 15/89* (2013.01)

(58) Field of Classification Search
CPC ........... B01L 2200/0668; C12M 33/04; C12M 35/00; A01K 67/0336; C12N 15/89
See application file for complete search history.

(56) References Cited

U.S. PATENT DOCUMENTS

| | | | |
|---|---|---|---|
| 2009/0254067 | A1 | 10/2009 | Kriesel |
| 2010/0263599 | A1* | 10/2010 | Yanik .................. G01N 33/5082 119/216 |
| 2014/0287509 | A1 | 9/2014 | Sharei et al. |
| 2015/0247790 | A1* | 9/2015 | Okumus ............ G01N 15/1463 506/12 |
| 2016/0016169 | A1* | 1/2016 | Ben-Yakar ........ B01L 3/502738 506/26 |
| 2018/0078940 | A1* | 3/2018 | Lee ...................... C12N 15/101 |
| 2019/0090458 | A1 | 3/2019 | Vayndorf et al. |

OTHER PUBLICATIONS

Abate, A.R., et al., Glass coating for PDMS microfluidic channels by sol-gel methods, Lab Chip, Apr. 2008;8(4):516-8.
Carlborg, C.F., et al., Beyond PDMS: off-stoichiometry thiol-ene (OSTE) based soft lithography for rapid prototyping of microfluidic devices, Lab Chip, Sep. 21, 2011;11(18):3136-47.
Fire, A., "Integrative transformation of Caenorhabditis elegans", EMBO J., Oct. 1986;5(10):2673-80.
Ghaemi, R., "Microfluidic device for microinjection of Caenorhabditis elegans", Masters Thesis, McMaster University, Hamilton, Ontario, Canada, 2014.
Gilleland, C.L., et al., "Computer-Assisted Transgenesis of Caenorhabditis elegans for Deep Phenotyping", Genetics, Sep. 2015;201(1):39-46.
Lockery et al., "Artificial Dirt: Microfluidic Substrates for Nematode Neurobiology and Behavior", J Neurophysiol, (Jun. 2008), vol. 99, No. 6, pp. 3136-3143, XP055666773.
McDonald, et al., "Fabrication of microfluidic systems in poly(dimethylsiloxane)", Electrophoresis, Jan. 2000;21(1):27-40.
Rolland, J.P., et al., Solvent-resistant photocurable liquid fluoropolymers for micorfluidic device fabrication, J Am Chem Soc, Mar. 3, 2004;126(8):2322-3.
Sollier, E., et al., Rapid prototyping polymers for microfluidic devices and high pressure injections, Lab Chip, Nov. 21, 2011;11(22):3752-65.
Song, P., et al., "A microfluidic device for automoated, high-speed microinjection of Caenorhabditis elegans", Biomicrofluidics, Feb. 26, 2016;10(1):011912.
WO/2020/005802 International Search Report.
Zhao, X., et alk., "Microfluidic chip-based C. elegans microinjection system for investigating cell-cell communication in vivo", Biosens Bioelectron, Dec. 15, 2013;50:28-34.

\* cited by examiner

MICROINJECTION CHIP, DEVICE, SYSTEM AND USES THEREOF FOR UNICELLULAR OR MULTICELLULAR ORGANISMS

CROSS-REFERENCE TO RELATED APPLICATIONS

This application claims the benefit of U.S. Provisional Patent Application No. 62/689,245, filed on 24 Jun. 2018, the content of which is incorporated herein by reference in its entirety.

STATEMENT REGARDING FEDERALLY SPONSORED RESEARCH OR DEVELOPMENT

This invention was made with government support under MH051383 awarded by the National Institute of Health. The government has certain rights in the invention

FIELD OF THE INVENTION

This application pertains generally to microfluidic devices and uses thereof for microinjection of biological reagents into organisms, embryos and/or cells.

BACKGROUND OF THE INVENTION

Microinjection of biological reagents into organisms, embryos, and cells is a fundamental and widely used method in research utilizing model organisms including nematodes, fruit flies, zebrafish, and mice in a growing number of applications. Typical reagents include DNA, RNA, peptides, proteins, and fluorescent markers. Typical applications include genetic transformation, gene knock-down, functional analysis of peptides and proteins, and lineage tracing. Under traditional methodology, each injection target is positioned, oriented, and stabilized by manual manipulation of single targets.

The traditional method for microinjection in *C. elegans* was first disclosed in 1986 (Fire A, EMBO J, 5:2673-80, 1986). In that method, a glass microinjection pipette is filled with the solution to be injected (injectant), for example a DNA solution, and mounted in a micromanipulator fixed to an inverted compound microscope. One to five adult nematodes are immobilized by placing them on a dry agarose pad formed on a microscope cover slip. A soft, flexible probe, for example an eyelash, is used to manipulate the nematodes into a parallel array, after which the nematodes are covered with halocarbon oil to reduce loss of fluid through evaporation. The coverslip is placed on a type of microscope stage that can be translated and rotated as needed to obtain the desired injection angle for the pipette. The pipette is then inserted into the target organ, for example the gonad, and injectant is dispensed by a brief pressure pulse applied to the lumen of the pipette. After each nematode has been injected, the nematodes are transferred to a culture plate, flooded with a physiological buffer solution, and allowed to recover.

That method has known disadvantages, which are overcome by the present microfluidic injection device. Those disadvantages include desiccation, limitation on the number of nematodes that can be injected per hour, and stress on both the organisms and investigator.

The agarose pad used in the conventional method desiccates the nematodes on the time scale of minutes. Desiccation is problematic because it can be fatal, reducing post-injection recovery rates and the overall success rate of genetic transformation. This problem limits the number of nematodes that can be immobilized and injected per coverslip. It also forces the user to work quickly, which can be stressful, reducing the number of nematodes that can be injected per user per day. Even experienced investigators rarely inject more than four to six different DNA constructs (80-120 nematodes) per day due to fatigue.

The conventional method uses a compound microscope, wherein nematodes are usually injected at relatively high magnification (e.g., 40×) and finding the next nematode to inject means raising the microinjection pipette, switching to a lower power objective with a wider field of view, moving the microscope stage to locate and reposition the next nematode, switching back to high magnification, and lowering the pipette. That series of operations can take several minutes per nematode, is error prone (e.g., the pipette may be broken), and adds to the fatigue experienced by the investigator. The conventional method requires extensive training, practice, and is time consuming to obtain a sufficient number of organisms with successful nucleic acid transformations.

The research literature contains four publications describing alternative methods for microinjection in *C. elegans* (Zhao X, Xu F, Tang L, Du W, Feng X, Liu B F. Microfluidic chip-based *C. elegans* microinjection system for investigating cell-cell communication in vivo. Biosens. Bioelectron. 2013 Dec. 15; 50:28-34; Gilleland C L, Falls A T, Noraky J, Heiman M G, Yanik M F. Computer-Assisted Transgenesis of *Caenorhabditis elegans* for Deep Phenotyping. Genetics. 2015 September; 201(1):39-46; Ghaemi, R. Microfluidic device for microinjection of *Caenorhabditis elegans*; Song P, Dong X, Liu X. A microfluidic device for automated, high-speed microinjection of *Caenorhabditis elegans*. Biomicrofluidics. 2016 Feb. 26; 10(1):011912). In all four cases, the nematodes remain hydrated throughout the procedure, an advantage as compared to the conventional method. Three of these methods utilize microfluidic channels to immobilize the nematodes (Zhao et al.; Ghaemi R.; and, Song et al.); the fourth immobilizes nematodes by means of a temperature-sensitive hydrogel that contains a toxic paralyzing agent, sodium azide (Gilleland et al.) Importantly, however, each of those methods relies on maintaining an unobstructed pathway from the environment to the nematode which complicates their use. Two methods involve nominally "closed" microfluidic chips in which the nematode is stabilized in an injection channel and the microinjection pipette is threaded through a side channel that is contiguous with the injection channel (Ghaemi, R.; Song et al.). The other two methods involve "open" systems in which the nematode is stabilized in a chamber that is open to the environment from above (Zhao et al.; Gilleland et al.). However, the nominally closed systems are actually open systems because the side channel through which the pipette passes is open to the environment.

Thus, there is a need for an improved microinjection device and methods. The present device disclosed herein positions, orients, and stabilizes microscopic injection targets by means of fluid-filled microfabricated channels that can be penetrated by microinjection pipettes; a truly closed system that provides advantages over known methods and devices for microinjection.

It is easier to integrate microinjection pipettes with the present microinjection chip than with the nominally closed systems in which the pipette must be threaded a long distance through a microchannel when changing pipettes, which frequently are defective or become clogged during injection. In one case, the injection pipette must be in place during the fabrication of the chip [Ghaemi, R]. This complicates the fabrication process and makes it impossible to change pipettes; instead, a new chip must be used.

The instant closed system microinjection chip comprises a sidewall, without an injection port, so that the microinjection pipette passes through the sidewall and reseals when the pipette is withdrawn, preventing leakage of fluid from the injection channel. In the nominally closed chips, a microfluidic valve is required to close the injection-pipette channel. Thus, active components requiring off-chip control apparatus are a necessity which complicates use of the nominally closed chips for many typical users.

The instant microinjection chip is adapted to restrain an organism by inserting it into a close-fitting injection channel. In open systems, by contrast, active restraint is required. In the method of Zhao et al., this is accomplished by capturing the nematode by means of a suction port as the nematode exits the inlet channel and enters the open chamber, again requiring active components and off-chip control apparatus. In the method Gilleland et al., wherein nematodes are restrained by a temperature-sensitive hydrogel, injections must be done at 25° C. which requires specialized environmental control over a large area, and the use of a paralytic agent which places a limitation on success rate.

The microinjection device disclosed herein addresses the deficiencies and technical challenges of the known microinjection devices and methods and provides an improvement for microinjection of biological reagents into microscopic organisms. The present microinjection device stabilizes the injection target in a fluid filled channel separated from the environment by a thin (e.g. 10 µm to 40 µm) side wall of microfluidic polymer (e.g. PDMS or other silicone polymers) that is easily penetrated by the microinjection pipette and resealed when the pipette is withdrawn.

SUMMARY OF THE INVENTION

Herein are provided microinjection chips, devices, systems and methods for injection of unicellular or multicellular organisms.

In embodiments, a microinjection chip comprises an inlet port, an injection channel, that does not comprise a microinjection port. and a post injection reservoir, wherein the inlet port, the injection channel and post injection reservoir are in fluid communication with each other wherein the inlet port is adapted to sequentially move individual organisms into the injection channel, which is adapted to immobilize the individual organism in fluid, and the injection channel comprises a side wall adapted to receive a microinjection pipette without a microinjection port and reseal when the microinjection pipette is removed.

In embodiments the height of the injection channel forces the organism to pass through the channel aligned in a singular line and in the case of a nematode the height of the injection channel, when less than the diameter of the nematode, forces nematodes onto their left or right lateral midlines in the channel. The organisms are passed through the injection channel by applied pressure to the inlet port by for example a syringe.

In embodiments, the side wall is formed from a material that allows the microinjection pipette to enter and be removed without forming an opening, and without breaking or clogging the microinjection pipette. In certain embodiments, the side wall has a thickness from 10 µm to 40 µm. In certain embodiments, the side wall comprises a silicone polymer or a thermoplastic polymer. In exemplary embodiments, the silicone polymer comprises a polydimethylsiloxane (PDMS) elastomer.

In embodiments, the unicellular or multicellular organism is an embryo or oocyte, fruit fly larva, a fish embryo or mammalian embryo. In exemplary embodiments, the multicellular organism is a nematode of any stage.

In embodiments, a microinjection device comprises a microinjection chip and backing bonded to the microinjection chip forming a bottom to the inlet port, injection channel and post injection reservoir. In certain embodiments, the backing comprises glass or plastic.

In embodiments, a microinjection system comprises a microinjection device and a microinjection pipette.

Disclosed herein are methods for microinjection of a liquid material into a unicellular or multicellular organism. In embodiments, the methods comprise adding a fluid comprising the unicellular or multicellular organism to the inlet port that is in fluid communication with an injection channel of a present microinjection device, placing the device comprising the unicellular or multicellular organism onto a stage of a microscope that comprises a micromanipulator and a microinjection pipette wherein the microinjection pipette is positioned in a resting position close to the side wall of the injection channel injecting the liquid material into the unicellular or multicellular organism by moving the micropipette comprising the liquid material through the side wall and penetrating the unicellular or multicellular organism that is stabilized in fluid within the injection channel, and removing the micropipette to the resting position and moving the unicellular or multicellular organism to the post injection reservoir. The unicellular or multicellular organism of the disclosed methods is suspended in an osmolarity adjusted buffer solution to reduce the internal hydrostatic pressure of the organism.

BRIEF DESCRIPTION OF THE DRAWINGS

In the drawings, like numerals describe similar components throughout the several views and different Figure numbers. The drawings illustrate generally, by way of example, but not by way of limitation, various embodiments disclosed herein. Unless otherwise specified, the dimensions measurements in the figures are in millimeters (mm)

FIG. 3C is a representation of the top plate 310 and bottom plate 305 prior to attachment to each other via the screws 345, and by screw 360 that fits through slot 365 of the top plate. FIG. 3D is a schematic views of an exemplary assembled brass mold. See Example 1.

DETAILED DESCRIPTION OF THE INVENTION

Introduction

Figure 1:
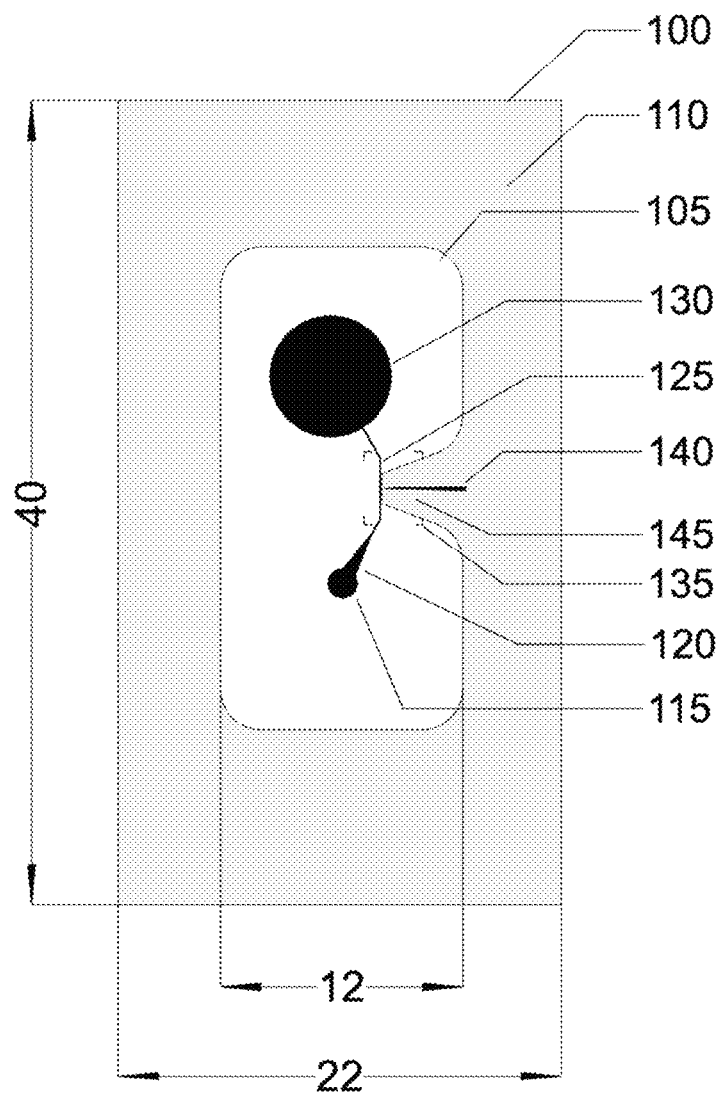
FIG. 1 shows a top view of an exemplary microinjection device 100. The microinjection chip 105 includes an inlet port 115 connected in series to a pre-injection reservoir 120, an injection channel 125 and a post-injection reservoir 130 with an outlet port. The microinjection chip 105 is secured to a backing 110 (e.g. glass coverslip).

Provided herein is a microinjection chip, device, system, and methods of use thereof for microinjecting unicellular or multicellular organisms. Microinjection of biological reagents into organisms, embryos, and cells is a fundamental and widely used method in research utilizing model organisms including nematodes, fruit flies, zebrafish, and mice in a growing number of applications. However, for traditional methodologies, each injection target is positioned, oriented, and stabilized by manual manipulation of single targets. The instant microinjection device or system, positions, orients, and stabilizes microscopic injection targets by means of fluid-filled closed microfabricated channels that can be penetrated by microinjection needles, also referred to herein as "microinjection pipettes".

In embodiments, the microinjection chip comprises four fluidic features, connected in series, molded into a silicone or thermoplastic polymer and closed with a backing such as a glass coverslip. Those fluidic features comprise an inlet port; a pre-injection reservoir, an injection channel, that does not comprise a microinjection port, and a post injection reservoir. The inlet port is adapted to sequentially move individual organisms into the injection channel, which is configured to immobilize the individual organism in fluid. The injection channel comprises a side wall adapted to receive a microinjection pipette without a microinjection port and reseal when a microinjection pipette is removed.

In embodiments, the side wall has a thickness from 10 μm to 40 μm and is formed from a material that allows the microinjection pipette to enter and be removed without forming an opening, and without breaking or clogging the microinjection pipette. That unique feature, along with an injection channel configured to hold an individual organism in fluid, provides advantages over known microinjection methods and is amendable to high throughput. The instant microinjection device stabilizes the injection target (e.g. organism) in a fluid filled channel separated from the environment by a thin side wall of a silicone polymer that is easily penetrated by the microinjection pipette. Unexpectedly, and as demonstrated in Example 2, the microinjection pipette was not broken or clogged by passing through the side wall.

In embodiments, the organism is a nematode. In exemplary embodiments, a microinjection device 100, comprising a microinjection chip 105 and backing 110, is filled with fluid by means of a syringe connected to the inlet port 115. The syringe is disconnected, and nematodes are loaded into the pre-injection chamber 120. In embodiments, the nematodes may be added individually from a culture plate using a nematode pick, or in bulk by injecting a fluid suspension of nematodes into the inlet port 115.

In certain embodiments, the microinjection device 100 is fitted into a frame 405 to form a microinjection device 400. In embodiments, a syringe is connected to the inlet port 115 and the microinjection device 400 secured to a compound microscope stage 505 configured with a micromanipulator 520 that holds an injection pipette 140 containing the injectant. In embodiments, a droplet of oil is placed in the nose-shaped cut-out 145 allowing a user to test the ability of the injection pipette to pass the correct amount of injection fluid when a pressure pulse is applied to the lumen of the microinjection pipette. The microinjection needle is then positioned in close apposition to the side wall 205 (resting position).

In embodiments, pressure from the syringe moves a single nematode from the pre-injection reservoir 120 to the injection channel 125 until the injection target, such as one arm of the nematode's gonad 605, is opposite the microinjection pipette. See FIG. 2A. In certain embodiments, the z position of the tip of the microinjection pipette is adjusted such that when it is advanced in the −x direction, it will penetrate the side wall 205, the nematode 210, and ultimately enter the injection target (e.g., a nematode gonad arm 605). In embodiments, the target (e.g., a nematode gonad arm 605) is injected and the microinjection pipette is withdrawn to the resting position. In embodiments, the microinjection pipette is withdrawn to a resting position within the side wall 205. In other embodiments, the microinjection pipette is withdrawn to a resting position outside of the sidewall 205.

Figure 6:
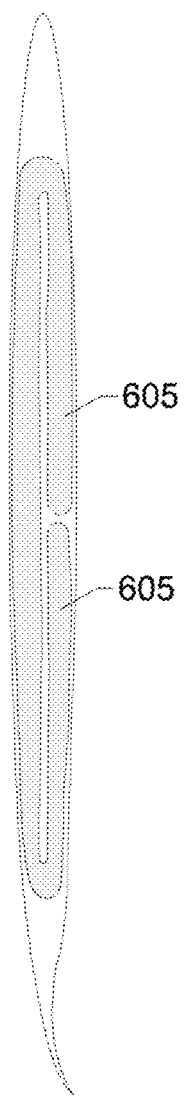
FIG. 6 shows a representation of a nematode with gonad arms 605.

In certain embodiments, it is desirable to inject a second target in the same nematode; for example, the second arm of the gonad 605 may be injected. See FIG. 6. In that instance, the nematode is moved slightly, and the injection process is repeated. Finally, the syringe connected to the inlet port 115 is used to move the injected nematode out of the injection channel 125 and into the post-injection reservoir 130. This action simultaneously brings the next nematode into the injection channel 125. The cycle of positioning, adjusting the height (e.g., z position of the pipette tip) of the microinjection pipette, and injecting the target is repeated until there are no more nematodes in the pre-injection reservoir 120. In embodiments, injected nematodes may be transferred to a culture plate, wherein the fluid containing the nematodes is pipetted from the post-injection reservoir 130 to a fresh culture plate.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, the term "fluidic device" refers to a device that utilizes the flow of fluid to distribute substances and/or organisms (such as substances dissolved in a fluid and/or substances or organisms suspended in a fluid). A fluidic device can be of any dimension, as long as its dimensions are suitable to accommodate the size of substances or organisms included or suspended in the fluid. In embodiments, a device is a microfluidic device that exploits the properties of fluid flow that arise at length scales in the sub-millimeter range. One such property is laminar flow. In some examples, a microfluidic device has a channel or chamber with at least one dimension of 300 microns or less. In other examples, two dimensions are 300 microns or less. Some microfluidic devices are fabricated in glass whereas others are fabricated in a bio-compatible silicone or thermoplastic polymer by replica molding. The latter are referred to as soft-lithography microfluidic devices. The term "microfluidic device" is sometimes used as a synonym for the more general term "microfabricated device," which refers to an object that may or may not exploit the properties of fluid flow at the sub-millimeter scale.

As used herein, the term "multicellular or unicellular organism" refers to a living being or system that are unicellular organisms (such as bacteria, protozoa, or fungi) or multicellular organisms (such as nematodes, trematodes, platyhelminths, insects, zebrafish, and non-human mammals).

As used herein, the term "target" is used to refer to the unicellular or multicellular organisms, or a specific organ or location within the organism, such as a gonad arm of a nematode; the nematode or the gonad arm, or both may be a "target".

All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Microinjection Chip, Device and System

In embodiments provided herein is a microinjection chip for injection of unicellular or multicellular organisms. In certain embodiments, the microinjection chip comprises an inlet port, an injection channel, that does not comprise a microinjection port and, a post injection reservoir, wherein the inlet port, the injection channel and post injection reservoir are in fluid communication with each other, wherein the inlet port is adapted to sequentially move individual organisms into the injection channel, which is adapted to immobilize the individual organism in fluid, and the injection channel comprises a side wall adapted to receive a microinjection pipette without a microinjection port and reseal when the microinjection pipette is removed.

In certain embodiments, the microinjection chip further comprises a backing and/or frame to increase the footprint to aid in ease of use to form a microinjection device. In embodiments, the microinjection device comprises a microinjection chip and a backing bonded to the microinjection chip forming a bottom to the microfluidic features—inlet port, injection channel and post injection reservoir. In embodiments, the backing comprises glass or plastic. In embodiments, the microfluidic device further comprises a frame, such as a frame that aides in use with a microscope stage.

In embodiments provided herein is a microinjection microfluidic system for microinjection of unicellular or multicellular organisms, wherein the system comprises a microinjection device, which comprises a microinjection chip, and a microinjection pipette.

In embodiments, the unicellular or multicellular organisms is an embryo or oocyte; a nematode of any development stage or a fruit fly larva; a fish or mammalian embryo. In exemplary embodiments, the organism is a nematode. The stage of the organism (e.g. embryo, oocyte, larva, or adult) is determined by the user and material to be injected using well know techniques in the art.

In embodiments, the material to be injected is a liquid material that comprises nucleic acid, chemical compounds, or enzymes in an aqueous solution. Chemical compounds that may be injected, include but are not limited to, peptides, proteins (such as antibodies), colored or fluorescent dyes, DNA, RNA, enzymes, hormones, neurotransmitters, neuromodulators, drugs, drug candidates, lipids, anthelmintic (compounds used to treat infection with parasitic worms, including roundworms (nematodes) and flatworms), subcellular organelles, or nanofabricated structures, including nano-materials (e.g. gold nanoparticles). Representative material that may be injected includes, but is not limited to: enzymes, including restriction enzymes for nucleic acid integration, polymerase, endonuclease; hormones, including growth hormones and growth factors; proteins, including fluorescent proteins, fluorescently labeled proteins, antibodies, including monoclonal antibodies that may, or may not, be a drug or drug candidate; peptides, including neuroactive peptides; nucleic acid molecules, including DNA plasmid constructs, mRNA molecules, tRNA molecules, synthetic mRNA molecules, RNA or RNAi molecules; neurotransmitters, including (but not limited to) acetylcholine, glutamate, gamma amino butyric acid; and, neuromodulators (but not limited to), including serotonin, dopamine, endorphins, and cannabinoids.

In certain embodiments, a microinjection chip is made from an elastomeric material such as a silicone polymer (for example, poly(dimethyl siloxane) (PDMS)). Suitable PDMS polymers include, but are not limited to Sylgard® 182, Sylgard® 184, and Sylgard® 186 (Dow Corning, Midland, Mich.). In one non-limiting example, the PDMS is Sylgard® 184. Polydimethylsiloxane (PDMS), also known as dimethylpolysiloxane or dimethicone, belongs to a group of polymeric organosilicon compounds that are commonly referred to as silicones. PDMS is viscoelastic, meaning that at long flow times (or high temperatures), it acts like a viscous liquid. However, at short flow times (or low temperatures), it acts like an elastic solid, similar to rubber.

In embodiments, the microinjection chip, including the sidewall, comprises PDMS or other mechanically similar viscoelastic silicone polymers. In alternative embodiments, the sideway comprises PDMS or other mechanically similar viscoelastic silicone polymers and other features of the microinjection chip comprise thermoplastic polymers.

Additional polymers that can be used to make the disclosed microinjection chip, provided a microinjection pipette can be moved through when cured, without breaking or clogging the pipette tip, include polyurethane, polyamides, polyethelyene, polycarbonates, polyacetylenes and polydiacetylenes, polyphosphazenes, polysiloxanes, polyolefins, polyesters (such as thermoset polyester (TPE)), polyethers, poly(ether ketones), poly(alkaline oxides), poly (ethylene terephthalate), poly(methyl methacrylate), polyurethane methacrylate (PUMA), polystyrene, thiol-enes, fluoropolymers (for example, perfluoropolyethers), Norland Optical Adhesive 81, and derivatives and block, random, radial, linear, or teleblock copolymers, cross-linkable materials such as proteinaceous materials and/or combinations of two or more thereof. Also suitable are polymers formed from monomeric alkylacrylates, alkylmethacrylates, alpha-methylstyrene, vinyl chloride and other halogen-containing monomers, maleic anhydride, acrylic acid, and acrylonitrile. Monomers can be used alone, or mixtures of different monomers can be used to form homopolymers and copolymers. See, e.g., U.S. Pat. No. 6,645,432; McDonald et al., *Electrophoresis* 21:27-30, 2000; Rolland et al., *J. Am. Chem. Soc.* 126:2322-2323, 2004; Carlborg et al., *Lab Chip* 11:3136-3147, 2011; Sollier et al., *Lab Chip* 11:3752-3765, 2011. In some examples, the channels of the device (such as a device made from PDMS) can be coated with a sol-gel. See Abate et al., *Lab Chip* 8:516-518, 2008, for example. In other embodiments, suitable materials for making the disclosed microfluidic chip include polymeric films, photoresist, hydrogels, or thermoplastic polymers.

In certain embodiments, a present microinjection chip comprises a silicone polymer or thermoplastic polymer. In exemplary embodiments, a silicone polymer comprises polydimethylsiloxane (PDMS) elastomer. In certain other embodiments, the thermoplastic polymers comprise poly(methyl methacrylate) (PMMA), polycarbonate (PC), polystyrene (PS), polyvinyl chloride (PVC), polyimide (PI), olefin polymers, cyclic olefin copolymer (COC), cyclic olefin polymer (COP), or cyclic block copolymer (CBC). In exemplary embodiments, the microinjection chip comprises PDMS.

FIG. 1 is a top view of one embodiment of a microinjection chip 105. The microinjection chip includes an inlet port 115, connected in series to a pre-injection reservoir 120, an injection channel 125 and post-injection reservoir 130. Fluid flows with cells or organisms, from the inlet port 115 via the pre-injection reservoir 120 into the injection channel 125 and exits via the post-injection reservoir 130. In exemplary embodiments, the width of the microinjection chip 105 is 12 mm and comprises PDMS. The microinjection chip 105 is bonded to a backing (e.g. glass coverslip) 110 to form a microinjection device 100. In exemplary embodiments, the length of the microinjection device 100 is 40 mm and the width is 22 mm.

Figure 2A:
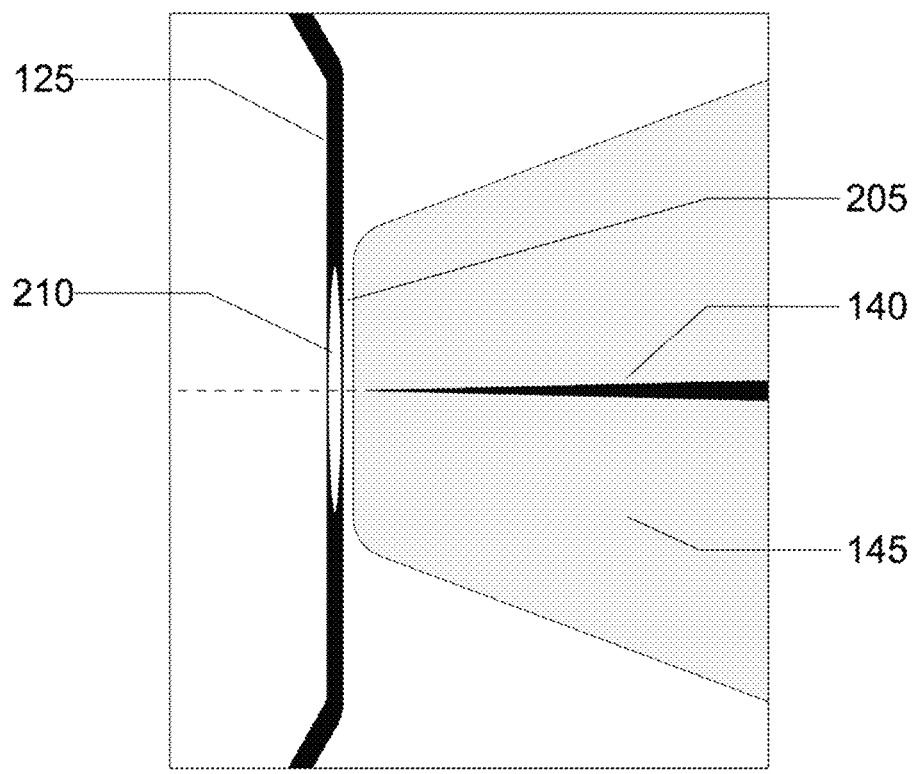
FIGS. 2A and 2B are an expanded view of 135 from FIG. 1 showing a nematode 210 in the injection channel 125 and microinjection pipette 140 resting near the side wall 205 in the nose-shaped cut-out 145, viewed from the top (FIG. 2A) and side (FIG. 2B) at the cross section indicated by the dashed line in FIG. 2A.
Figure 2B:
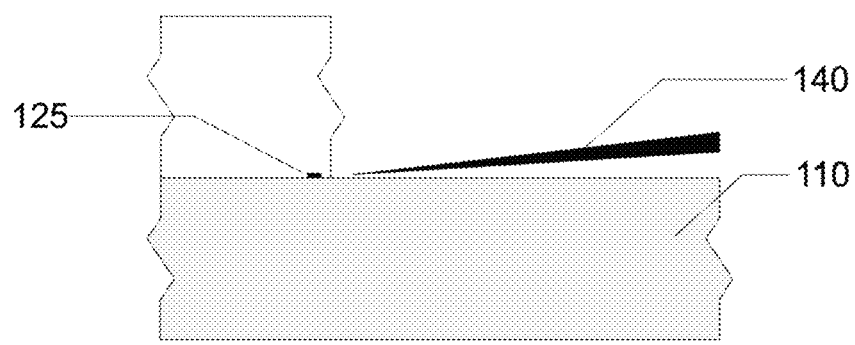

FIG. 2A is a top view of one embodiment of the microinjection chip showing an expanded view of a nose-shaped cut-out 145. This view shows the side wall 205, which is thin enough to allow a microinjection pipette 140 to pass through without breaking or clogging, the injection channel 125, a nematode 210 in the injection channel 125 and the microinjection pipette 140 in a resting position near the side wall 205. FIG. 2B is a cross section view corresponding to the dashed line of FIG. 2A showing the injection channel 125, side wall 205, microinjection pipette 140 and backing 110.

In embodiments, the side wall has a thickness from 10 μm to 40 μm. In certain embodiments, the side wall has a thickness of about 10 μm, about 11 μm, about 12 μm, about 13 μm, about 14 μm, about 15 μm, about 16 μm, about 17 μm, about 18 μm, about 19 μm, about 20 μm, about 21 μm, about 22 μm, about 23 μm, about 24 μm, about 25 μm, about 26 μm, about 27 μm, about 28 μm, about 29 μm, about 30 μm, about 31 μm, about 32 μm, about 33 μm, about 34 μm, about 35 μm, about 36 μm, about 37 μm, about 38 μm, about 39 μm or about 40 μm. In other embodiments, the side wall has a thickness from about 10 μm to about 35 μm, from about 10 μm to about 30 μm, from about 10 μm to about 25 μm, or from about 10 μm to about 20 μm. In certain other embodiments, the side wall has a thickness from about 15 μm to about 40 μm, from about 20 μm to about 40 μm, from about 25 μm to about 40 μm, or from about 30 to about 40 μm.

In embodiments, the side wall is formed from a material that allows the microinjection pipette to enter and be removed without forming an opening, and without breaking or clogging the microinjection pipette. Those materials include any of the above disclosed viscoelastic polymers for the microinjection chip composition. In embodiments, the side wall is formed from a silicone polymer. In exemplary embodiments, the side wall is formed from PDMS.

Microfluidic devices, such as the present microinjection chip, can be fabricated by methods known to one of ordinary skill in the art. In some examples the disclosed devices are made by molding uncured polymer from a photoresist master using standard photolithographic methods (e.g., U.S. Pat. No. 6,645,432; Madou, Fundamentals of Microfabrication, CRC Press, Boca Raton, Fla., 1997). In other examples, the disclosed devices are made by chemical etching, laser cutting, photopolymerization, lamination, embossing, or injection molding. One of ordinary skill in the art can select an appropriate fabrication method based on the selected material for the device.

Figure 3A:
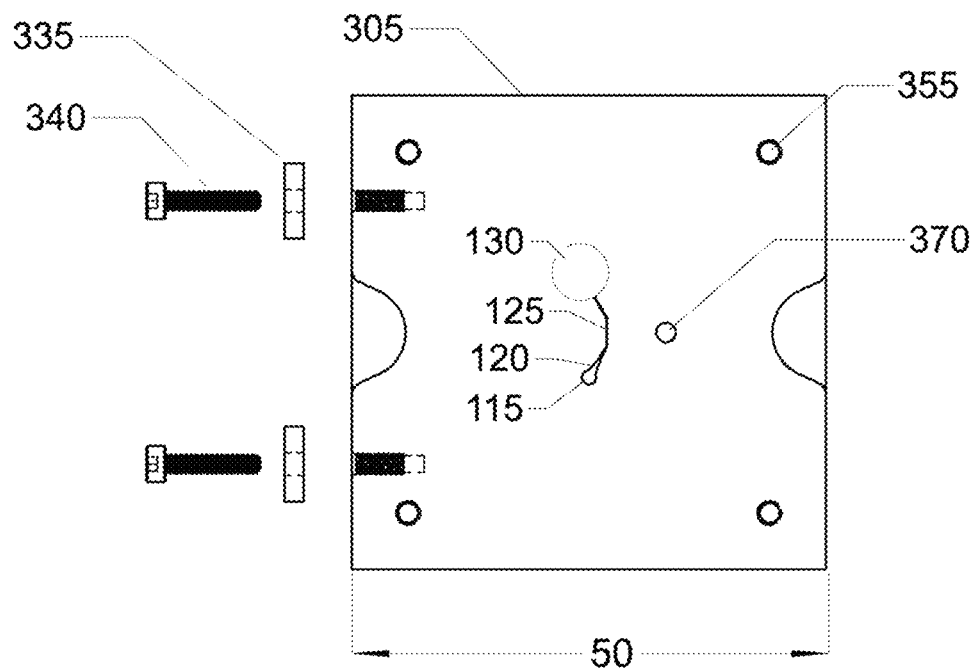
FIGS. 3A-3D are schematic views of a mold device used to manufacture the microinjection chip 105. A bottom plate 305 (FIG. 3A) and top plate 310 (FIG. 3B) form the mold. The mold includes a central opening 315, a nose-shaped cut-out 145, a curvilinear channel 320, screws 340 that secure washers 335 that facilitate correct alignment of the top and bottom plates and slot 365 to stabilize the nose-shaped cut-out 145 with screw 360 when the mold is assembled. Clearance holes 350 and 365 in the top plate 310, and corresponding threaded holes 355 and 370 in the bottom plate 305, accept screws 345 and 360, respectively. The microfluidic features are represented, in negative, on the bottom plate 305 as the inlet port 115, pre-injection reservoir 120, injection channel 125 and post-injection reservoir 130.
Figure 3B:
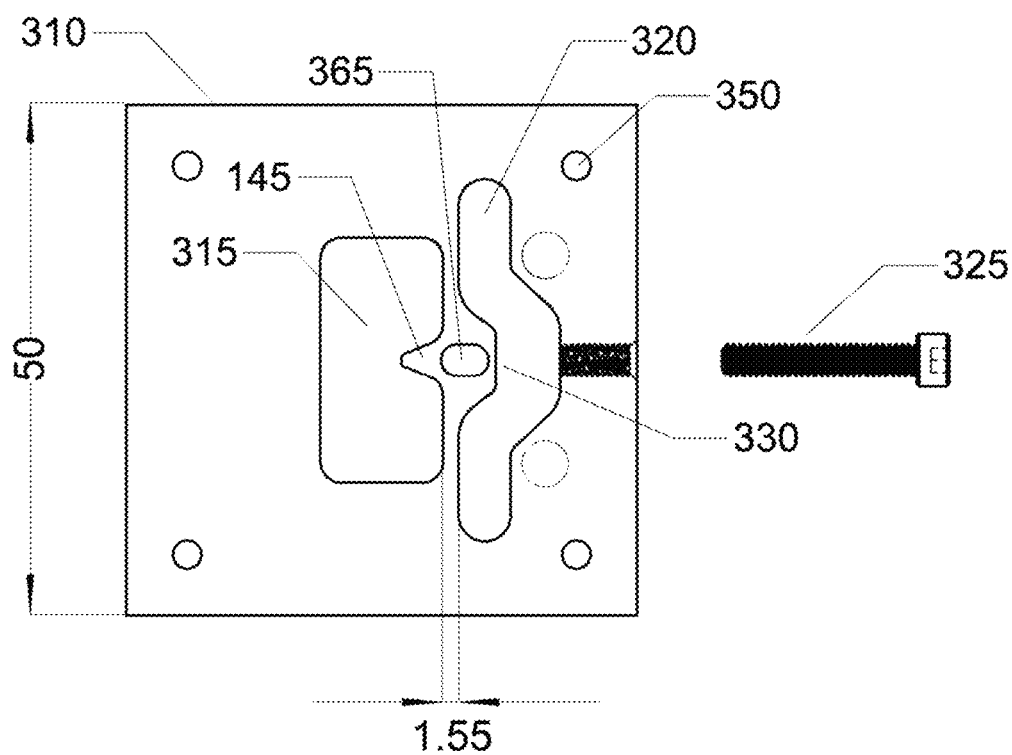

In exemplary embodiments, microinjection chip 105 was fabricated with PDMS using a metal alloy mold, preferably a brass mold, with a top plate 310 and bottom plate 305 wherein the microfluidic features were formed by micromachining the top surface of the bottom plate. FIG. 3A is a top view of the bottom plate 305 including the microfluidic features, the inlet port 115, pre-injection reservoir 120, injection channel 125 and post-injection reservoir 130. The other features of the bottom plate are used to secure the top plate 310 to the bottom plate 305, and include threaded holes 355 and 370, screws 340 and washers 335. An exemplary width of the bottom plate 305 is 50 mm. FIG. 3B is a top view of a complementary, and exemplary, top plate 310 that includes a central opening 315, which forms the footprint of the microinjection chip 105, and the curvilinear channel 320, which aids in obtaining the correct thickness of the side wall 205. In exemplary embodiments, the width between the central opening 315 and curvilinear channel 320 is 1.55 mm. An exemplary width of the bottom plate 305 is 50 mm.

Figure 3C:
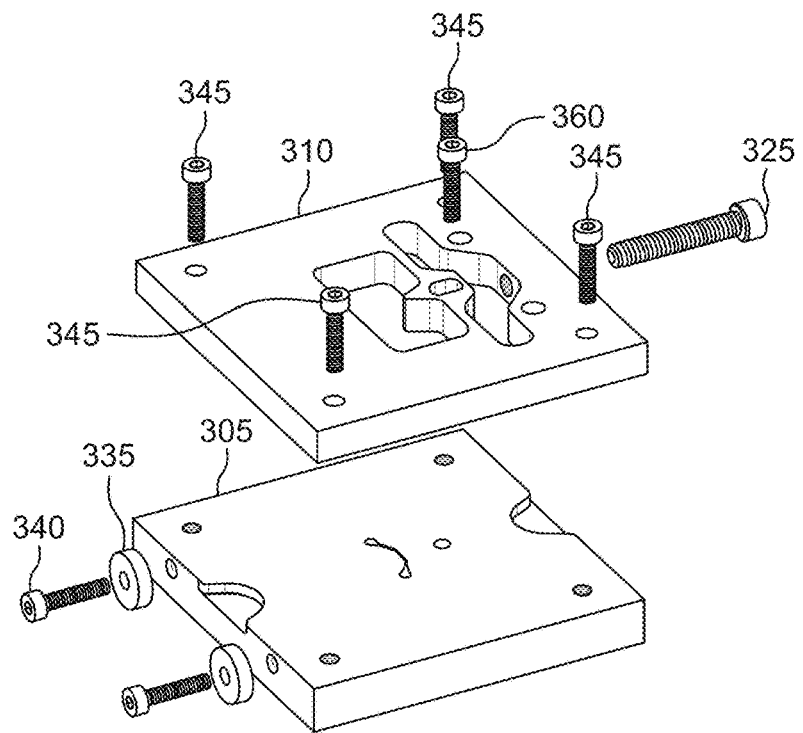
Figure 3D:
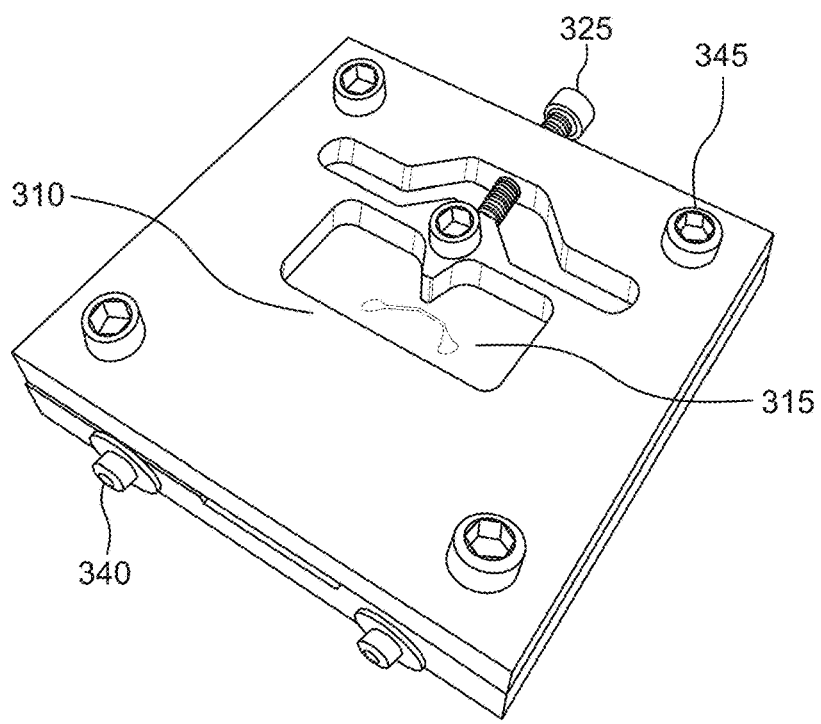

FIG. 3C is an angled top view of the top plate 310 and bottom plate 305 just prior to assembly, wherein screws 345 are fitted through clearance holes 350 of the top plate 310 and secured into threaded holes 355 of the bottom plate 305. The nose-shaped cut-out 145 can be adjusted to ensure the correct thickness of the side wall 205 by use of screw 325 threaded into the corresponding hole in the edge of the top plate 310 (not shown) until it contacts the back end 330 of the feature that will form the nose-shaped cut-out 145. To maintain that positioning, screw 360 is placed through slot 365 of the top plate 310 and into the corresponding threaded hole 370 on the bottom plate 305. Once assembled, as shown in FIG. 3C, polymer can be placed in the central opening 315 and cured to form a microinjection chip 105. See Example 1.

In alternative embodiments, the present microinjection chips may be fabricated using replica molding. This method involves make a negative mold of the microinjection chip. In embodiments, the mold may be fabricated with a polyurethane (PU) casting material (as compared to a brass mold of FIG. 3). In embodiments, the replica mold can be cast against multiple PDMS microinjection chips, such as six PDMS microinjection chips.

In embodiments, the manufactured microinjection chip is bonded to a backing to form a microinjection device, wherein the backing forms the bottom of the microfluidic features creating a closed injection channel. The inlet port, and port to the post-injection reservoir, are formed after the polymer is cured, such as with a biopsy punch. In embodiments, a microinjection device comprises a microinjection chip comprising an inlet port, an injection channel, that does not comprise a microinjection port, and a post injection reservoir, wherein the inlet port, the injection channel and post injection reservoir are in fluid communication with each other; wherein the inlet port is adapted to sequentially move individual organisms into the injection channel, which is adapted to immobilize the individual organism in fluid, and the injection channel comprises a side wall adapted to receive the microinjection pipette without a microinjection port and reseal when the microinjection pipette is removed and, a backing bonded to the microinjection chip forming a bottom to the inlet port, injection channel and post injection reservoir. In embodiments, the backing comprises glass or plastic. Exemplary microinjection devices include device 100 and device 400.

Figure 4A:
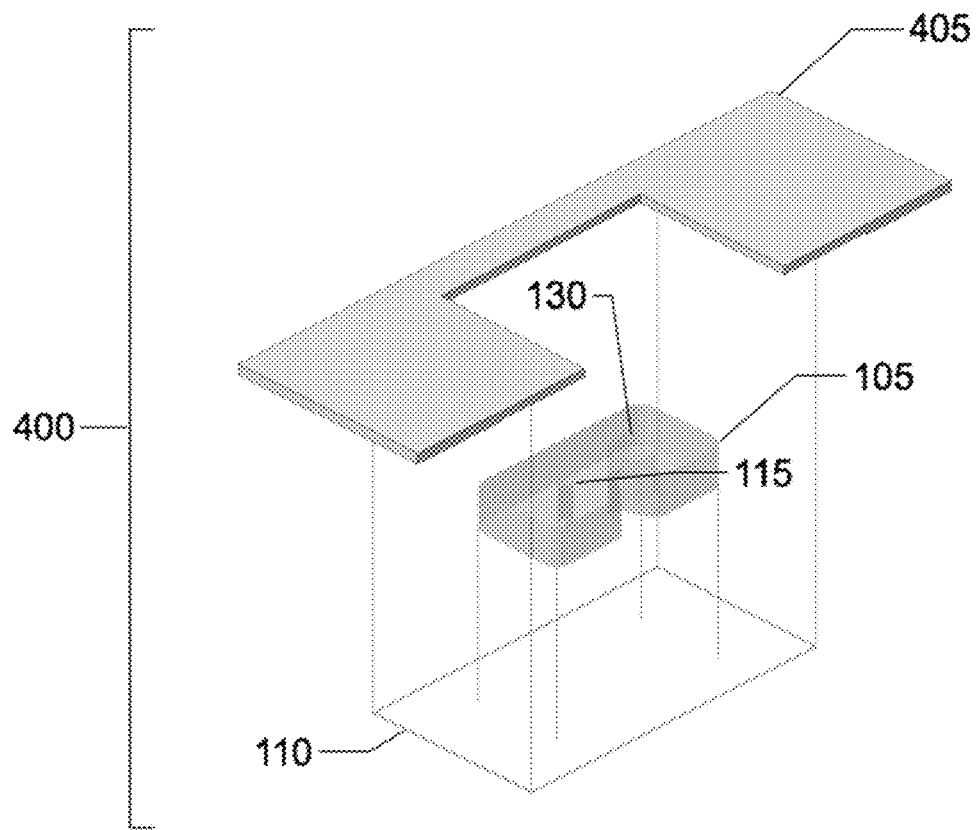
FIG. 4A shows an exemplary microinjection device 400 including a frame 405, the microinjection chip 105 and backing 110 (e.g., glass coverslip) and featuring an inlet port 115 and post injection reservoir 130; and, FIG. 4B is a schematic view of an exemplary microinjection device 400 that includes a frame 405, microinjection chip 105 and backing 110.
Figure 4B:
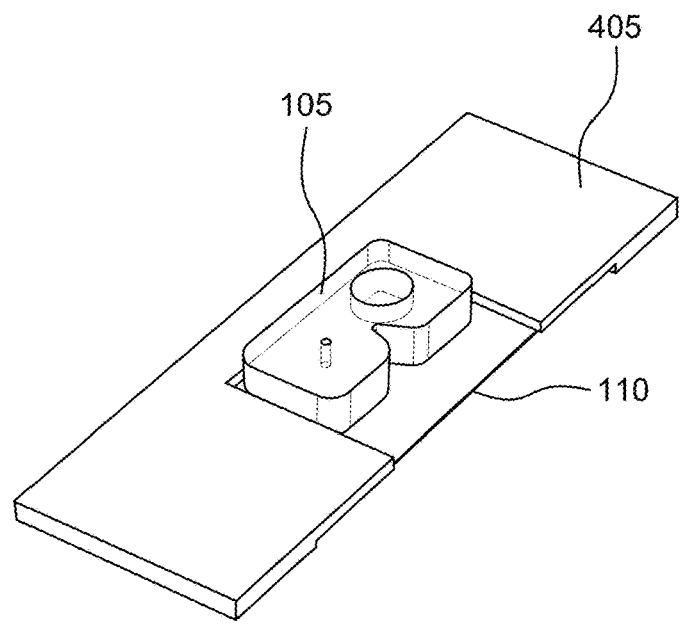

In other embodiments, a microinjection device further comprises a frame that holds the microinjection device 100 forming the device 400. FIG. 4A is an angled top view of a frame 405 placed around three sides of the microinjection chip 105, featuring an inlet port 125 and post injection reservoir 130, and over the backing 110 that extends beyond the microinjection chip 105. FIG. 4B is an exemplary microinjection device 400 comprising microinjection device 100 and a frame 405. Microinjection device 100 is a microinjection chip comprising microfluidic features inlet port, pre-injection reservoir, injection channel and post injection reservoir, and comprising a backing.

In embodiments, a present microinjection device is combined with a microinjection pipette to form a system for microinjection of unicellular or multicellular organisms. In embodiments, a present system comprises a microinjection pipette and a microinjection device that comprises an inlet port, an injection channel, that does not comprise a microinjection port, and a post injection reservoir, wherein the inlet port, the injection channel and post injection reservoir are in fluid communication with each other; wherein the inlet port is adapted to sequentially move individual organisms into the injection channel, which is adapted to immobilize the individual organism in fluid, and the injection channel comprises a side wall adapted to receive the microinjection pipette without a microinjection port and reseal when the microinjection pipette is removed, and a backing bonded to the microinjection chip forming a bottom to the inlet port, injection channel and post injection reservoir. Microinjection pipettes are well known, and comprise glass or quartz capillary tubes, with or without an internal filament as an aid to filling with fluid, having micron or sub-micron sized tips formed by heating and drawing the tube. Tip sizes may be further adjusted by breaking or beveling the tip.

Figure 5A:
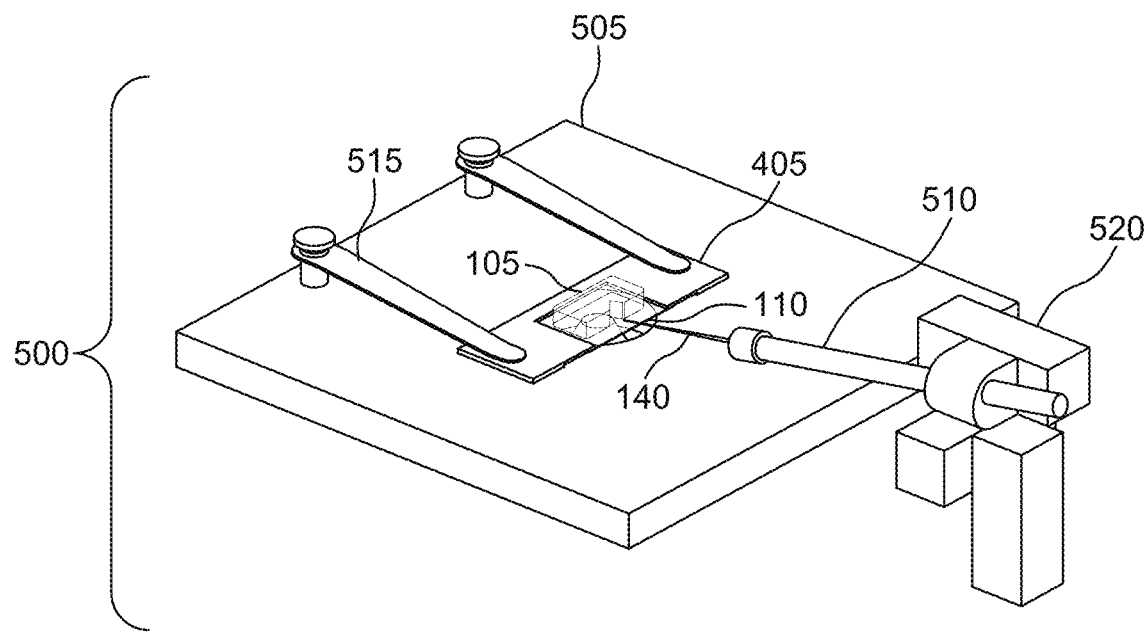
FIG. 5A shows an exemplary microinjection system 500 that includes a microinjection device 400, featuring the microinjection chip 105, backing 110 and frame 405, on a microscope stage 505, held in place by clips 515, with a micropipette holder 510, micromanipulator 520 and microinjection pipette 140; and, FIG. 5B is a schematic view of an exemplary microinjection system 500.
Figure 5B:
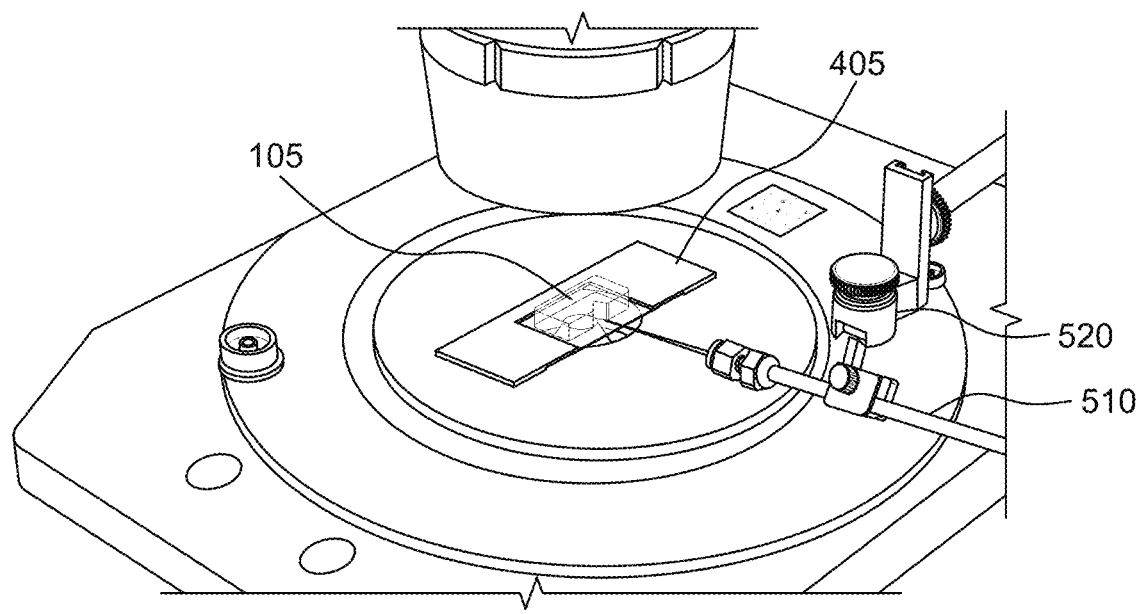

In embodiments, the microinjection system further comprises a compound microscope and components of the microscope, as well as a pressure injector, pressure regulator, micropipette holder and micromanipulator. FIG. 5A is a view of an exemplary microinjection system 500 featuring microinjection device 400, comprising microinjection chip 105 and backing 110, placed on a microscope stage 505, wherein the device 400 is held in place with clips 515. A micromanipulator 520 operationally connected to a micropipette holder 510 aids in positioning the microinjection pipette 140 to a resting position and during injections. FIG. 5B features an exemplary microinjection system 500.

Methods

In embodiments, are methods for using a microinjection chip, device and/or system for microinjection of a liquid material into a unicellular or multicellular organism. In embodiments, steps of the method include adding a fluid that contains the unicellular or multicellular organism to the inlet port of a present microinjection chip, device and/or system, wherein the inlet port is in fluid communication with an injection channel; placing the present microinjection chip or device comprising the unicellular or multicellular organism onto a stage of a microscope that includes a micromanipulator and microinjection pipette that is positioned in a resting position close to the side wall of the injection channel; injecting the liquid material from the micropipette into the unicellular or multicellular organism by moving the micropipette, using the micromanipulator, and inserting the tip of the micropipette through the side wall of the microinjection chip and penetrating the unicellular or multicellular organism that is stabilized in fluid within the injection channel; moving the micropipette to the resting position; and moving the unicellular or multicellular organism to the post injection reservoir. In embodiments, the fluid containing the unicellular or multicellular organism further includes a buffer. To assure the survivability of the organism the osmolarity of the buffer solution is adjusted to reduce the internal hydrostatic pressure of the organism. For example, the osmolarity of the buffer solution is adjusted to 350 mOsm by the addition of a glycerol solution to a phosphate buffer (pH 7.1) that includes potassium, magnesium sodium and sulfate ions. The reduced internal hydrostatic pressure of the animals limits the extent of herniation through the hole in the body wall made by the microinjection pipette.

The organisms which are effectively injected are separated from the organism that could not be, or were not, injected due to for example not being positioned optimally, in order to optimize the workflow and reduce unnecessary work up of defective organisms. The non-injected nematodes can be eliminated from further handling by the following exemplary methods. In a first method, the non-injected nematode's shell-like layer covering the body, is disrupted mechanically fragmenting the nematode. This is accomplished by advancing the injection pipette through the nematode until its tip reaches the opposite side of the injection channel and pushing the nematode out of the channel by applying pressure to the syringe attached to the inlet port. In a second method, a soluble fluorescent molecule is added to the injection fluid placed in the injection needle. For example, fluorescein or rhodamine may be added to a DNA mixture. After an injection run, organisms are sorted by fluorescence, and only the fluorescent organisms are retained in the down-stream workflow.

In embodiments, the inlet port, the injection channel and post injection reservoir are in fluid communication with each other and include a buffer solution. The method further includes the use of a syringe attached to the inlet port to move unicellular or multicellular organism from the inlet port to the injection channel and into the post injection reservoir. See Example 2. In certain embodiments, the method further includes applying pressure to the inlet port to move unicellular or multicellular organisms from the inlet port to the injection channel and into the post injection reservoir. In embodiments, applying pressure is performed using a syringe, a pump or compressed air. In embodiments, the step of injecting liquid material is repeated until all organisms added to the inlet port have been injected, wherein individual organisms are moved from the pre-injection reservoir, injection channel and finally into the post injection reservoir via pressure applied at the inlet port. In exemplary embodiments, a syringe is used to move the organisms through the microfluidic features for injection and to the post injection reservoir.

In embodiments the liquid material to be injected is any of the liquid materials disclosed herein and comprising nucleic acid, chemical compounds, or enzymes in an aqueous solution. In embodiments, the liquid material comprises nucleic acid plasmid constructs, enzymes, peptides, proteins, fluorescent dyes, or markers.

EXAMPLES

The following examples are put forth so as to provide those of ordinary skill in the art with a complete disclosure and description of how to use the embodiments provided herein and are not intended to limit the scope of the disclosure nor are they intended to represent that the Examples below are all of the experiments or the only experiments performed. Efforts have been made to ensure accuracy with respect to numbers used (e.g. amounts, temperature, etc.) but some experimental errors and deviations should be accounted for. Unless indicated otherwise, parts are parts by volume, and temperature is in degrees Centigrade. It should be understood that variations in the methods as described can be made without changing the fundamental aspects that the Examples are meant to illustrate.

Example 1: Design and Fabrication of the Device

Provided herein is a microinjection device for injection of unicellular or multicellular organisms. See FIGS. 1 to 5.

Provided herein is the design and fabrication of the microinjection device and system represented in FIGS. 1 to 5. The microinjection device was prepared with a rectangular polydimethylsiloxane (PDMS) block (e.g., microinjection chip) 105 measuring 12 mm×24 mm×4.85 mm bonded to a No. 1 cover slip 110 measuring 22 mm×24 mm×0.160 mm. Four fluidic features, 0.025 mm high, and connected in series, were molded into the bottom of the block: (i) a 1.5 mm diameter circle which formed the bottom of the inlet port 115, (ii) a triangular chamber with a base of 0.75 mm and a length 2.2 mm which served as pre-injection reservoir 120, (iii) an injection channel 0.075 mm wide and 3.0 mm long 125, which stabilized the nematode, and (iv) a 6.0 mm diameter circle which formed the bottom center of the outlet port (e.g. post injection reservoir) 130. Inlet and outlet ports were created by forming circular channels extending vertically from the top surface of the microinjection chip 105 to the bottom. Diameters of the inlet and outlet ports were 1.5 and 6.0 mm, respectively. Referring to the area of detail 135, represented by FIG. 2A, the width of the exterior side wall 205 of the injection channel 125 was reduced to 0.010-0.040 mm to facilitate alignment of the microinjection pipette 140 with the injection target and to shorten the distance through which the pipette tip must travel through PDMS to reach the nematode 210. The width of the side wall was reduced by molding a nose-shaped cut-out 145 into the PDMS block.

To form the PDMS block, we created a square, two-piece brass mold comprising a bottom plate 305 (FIG. 3A) and a top plate 310 (FIG. 3B) with a side length of 50 mm. The top and bottom plates were 4.85 mm and 6.21 mm thick, respectively. The four fluidic features (115, 120, 125, 130), in negative, were formed by micromachining the top surface of the bottom plate. The top plate contained a central opening 315 which formed the footprint of the PDMS block (e.g., microinjection chip), including the nose-shaped cut-out 145. The depth of the central opening 315, determined by thickness of the top plate, defined the height of the PDMS block (e.g., microinjection chip). The top plate contained a curvilinear channel 320 located as close as 1.55 mm to the central opening, and parallel to its long axis. The distance between the broad point of the nose-shaped cut-out 145 and the nematode injection-channel feature 125 could be adjusted by means of a 5-40×0.75 in. screw 325 which could be brought into contact with the back end 330 of the nose-shaped feature 145. We assembled the mold by placing the top surface of the bottom plate in contact with the bottom surface of the top plate. See FIG. 3C. Course positioning of the nose-shaped feature 145 with respect to the injection channel feature 125 was facilitated by means of washers 335 attached by M2×10 mm screws 340 inserted into one edge of the bottom plate. The two plates were joined by four M3×10 mm screws 345 passing through clearance holes 350 in the four corners of top plate and inserted into threaded holes 355 in the corners of the bottom plate. After assembling the plates, we advanced the screw 325 until the broad point of the nose-shaped cut-out 145 was 0.010-0.040 mm from the injection-channel feature 125, as judged by eye while the mold was viewed at 60× magnification on a stereomicroscope. The nose-shaped cut-out 145 was clamped firmly to the bottom plate by means of an M3×10 mm screw 360 inserted through a slot 365 the top plate and into threaded hole 370 in the bottom plate. We found this step to be essential to prevent PDMS prepolymer from seeping under the nose-shaped feature 145 during casting.

Polydimethylsiloxane (PDMS, Dow Corning) prepolymer was mixed in the weight ratio 10:1 (prepolymer to curing agent), degassed, and poured into a 20 mL syringe. Placing the mold on a balance, we deposited 1.32 g of PDMS prepolymer into the central opening 315 of the mold. This amount of prepolymer ensured that there was neither a positive nor a negative meniscus at the edges of the top of the block, yielding an optically flat PDMS surface which provided uniform illumination of the organism in the injection channel. The PDMS prepolymer was cured for 45 minutes at 150 C by placing the mold on a hotplate. After cooling the mold on a damp sponge, we disassembled the mold to release the PDMS block (e.g. microinjection chip) 105. The inlet port 115 and post-injection reservoir 130 were formed using 1.5 mm and 6.0 mm biopsy punches, respectively. For bonding, the coverslip 110 and the PDMS block 105 were cleaned and activated by placing both parts in an air plasma (medium field strength, PDC-32G plasma cleaner, Harrick Plasma, Inc., USA) for 1 minute and immediately bringing the coverslip 110 into contact with the feature side of the PDMS block 105. Curing of the bond was accelerated by baking the device for 30 minutes at 100 C. Finally, the assembled device was glued into place in a 25 mm×75 mm aluminum frame 405 using cyanoacrylate adhesive.

The dimensions of the microinjection device may be adapted, increased or decreased in size, to accommodate uni- or multi-cellular organisms of various sizes.

Example 2: Methods of Microinjecting Nucleic Acid into Nematodes

Provided herein is a method for microinjecting nematodes using the microfluidic device designed and fabricated in Example 1.

To obtain nematodes of a consistent size that were compatible with the dimensions of the injection channel 125, we utilized a common procedure to obtain a large number of age synchronized eggs. This involved dissolving gravid hermaphrodites in a bleaching solution, the ingredients of which are shown in Table 1. Eggs were deposited in a culture plate containing food and cultivated at 15° C. for 5 days, yielding a large population of young adult nematodes.

TABLE 1

| Bleaching Solution | |
|---|---|
| Constituent | Amount (mL) |
| Distilled water | 3.675 |
| Sodium hypochlorite solution (5%) | 1.200 |
| NaOH solution (10M) | 0.125 |

Alternative methods using filters can also be used to obtain an age/size synchronized population of nematodes for injections. See US Patent Publ. No. 2019/0090458.

To prepare the microfluidic device for injections, we filled a 5 mL syringe with M9 buffer solution defined in Table 2. The osmolarity of the buffer solution was adjusted to 350 mOsm by addition of 0.14 mL of a 100% glycerol solution per 10 mL of buffer. We made this adjustment to reduce the internal hydrostatic pressure of the animals, thereby limiting the extent of herniation through the hole in the body wall made by the microinjection pipette. The syringe was fitted with a 50 cm length of polyethylene tubing (1.4 mm ID, 1.9 mm OD), with a stainless-steel tube (1.2 mm ID, 1.47 mm OD, 12.7 mm long) inserted halfway into the open end. The microfluidic device was filled with buffer solution by inserting the stainless-steel tube into the inlet port 115 and ejecting an amount of solution sufficient to fill the injection channel. After removing the tubing from the device, a small amount of buffer solution was deposited over the inlet port, yielding a hemispherical droplet.

TABLE 2

| M9 Buffer Solution (pH 7.1) | |
|---|---|
| Constituent | Amount |
| $KH_2PO_4$ | 3 g |
| $Na_2HPO_4$ | 6 g |
| NaCl | 5 g |
| $MgSO_4$ (1M) | 1 mL |
| Distilled water | to 1 L |

To transfer nematodes to the microinjection device, a culture plate containing young adult nematodes grown from synchronized eggs was filled to a depth of 5 mm with the M9 buffer solution (Table 2) and swirled to lift nematodes into the solution. While alternately viewing the culture plate and microfluidic device under a stereomicroscope, we lifted individual nematodes from the suspension using an eyelash glued to a toothpick and transferred them to the droplet over the inlet port until 20-30 nematodes had been added to the droplet. As nematodes are denser than the buffer solution, they quickly sank to the bottom of the inlet port. At this point, we reinserted the tubing into the inlet port and placed the microfluidic device on the microscope stage 505 of a microinjection workstation comprised of the components listed in Table 3. The microfluidic device was oriented perpendicular to the axis of the microinjection pipette 140 when the pipette was inserted into the microinjection pipette holder 510. The microfluidic device was clamped to the stage by specimen clips 515. The micropipette holder was held in a micromanipulator 520 for fine positioning of the microinjection pipette. Microinjection pipettes having an outside diameter of approximately 0.5-1.0 µm at the tip were fabricated on a conventional micropipette puller using conventional 0.58 mm ID, 1.00 mm OD borosilicate glass capillaries containing a filament. In some cases, this pipette tip was widened by touching it against the edge of the cover slip 110 to break it.

TABLE 3

| Microinjection Workstation Components | | |
|---|---|---|
| Item | Model | Supplier |
| Inverted compound microscope | MINJ-1000 | Tritech Research |
| Pressure injector | MINJ-D | Tritech Research |
| Microscope stage | MINJ-GS | Tritech Research |
| Pressure regulator | TREG-N2 | Tritech Research |
| Micropipette holder | MINJ-4 | Tritech Research |
| Micromanipulator | MMO-202ND | Tritech Research |

To begin injections, the tip of microinjection pipette was positioned near the center of the injection channel, approximately 10 microns away from the side wall 205 of the microfluidic device. The height of the tip was adjusted to coincide with the vertical center of one of the nematode's gonad arms 605, the optimal DNA injection site. For each injection, we moved an individual nematode to the center of the injection channel by pressure from the syringe while viewing the channel with a 40× microscope objective. The height of the injection channel, being less than the diameter of the nematode, together with normal dorso-ventral flexions associated with crawling, forced nematodes onto their left or right lateral midlines in the channel. In this orientation the gonad arms came to rest near one or the other side walls of the channel. Injections were performed only on those nematodes in which the gonad arms were near the exterior side wall of the microfluidic device.

Initially, nematodes in which the gonad arms were on the opposite side were rejected by moving them into the post-injection reservoir 130. However, we found that in situations where the proportion of non-injected nematodes would create an undue burden on down-stream workflows, non-injected nematodes could be eliminated from further handling by either of two methods. In the first method, the non-injected nematode's cuticle, the soft, shell-like layer covering the body, is disrupted mechanically. This is accomplished by advancing the injection pipette through the nematode until its tip is inserted into the PDMS wall on the interior side of the channel. Then, with the injection pipette in this position, the nematode is pushed out of the channel by applying pressure to the syringe attached to the inlet port. This procedure fragments the nematode. In the second method, a soluble fluorescent molecule is added to the DNA mixture placed in the injection needle. In one example, fluorescein dextran is added to the DNA mixture at a concentration of (2.5 mg/mL); in another example, tetramethylrhodamine is added to the injection mixture at a concentration of (1.25 mg/mL). After an injection run, nematodes are sorted by fluorescence, and only the fluorescent nematodes are retained in the down-stream workflow.

For nematodes in the correct orientation in the injection channel, DNA was injected by advancing the tip of the microinjection pipette through the exterior side wall and into the gonad arm, then applying one or more pressure pulses of 30-70 psi for approximately 0.5 sec. In general, we injected both gonad arms before moving to the next nematode. Injected (and killed or non-fluorescent non-injected) nematodes were recovered from the microfluidic device by withdrawing all the fluid in the post-injection reservoir with a glass Pasteur pipette. Each recovered nematode was placed on its own culture plate and allowed to reproduce for 4-6 days, meaning approximately 2-3 generations, at which point offspring were examined for expression of injected DNA.

Successful operation of the device was demonstrated by injecting a circular DNA construct containing a genetically dominant allele (su1006) of the gene rol-6 into nematodes from the reference strain N2. Expression of this allele causes a defect in the outer surface of the nematode's body wall that forces the nematode to crawl in tight circles, an easily detectable phenotype called "roller," which served as a marker for a successful DNA injection. For this demonstration the microinjection pipette contained 40 ng/ul of the rol-6 construct mixed with 60 ng/ul of filler in the form of sonicated salmon testis DNA. The success rate r for DNA injections was defined as $r=N_T/N_I$, where $N_T$ is the number nematodes having roller progeny and $N_I$ is the number of nematodes injected. In 3 trials, r ranged from 0.27-0.70, with a mean r value of 0.5±0.18 standard deviations.

What I claim is:

1. A microinjection device for injection into unicellular or multicellular organisms, comprising a microinjection pipette, a microinjection chip and a backing bonded to the microinjection chip wherein the microinjection chip is molded and monolithic comprising, in fluid communication with each other:
   a) an inlet port comprising an exterior side wall having a first width;
   b) a preinjection reservoir;
   c) an injection channel that does not comprise a microinjection port and comprises an exterior sidewall having a second width less than the first width, wherein the exterior side wall of the injection channel has a thickness from 10 μm to 40 μm and wherein the microinjection pipette is positioned adjacent to the exterior side wall for injection; and,
   d) a post injection reservoir comprising an exterior side wall having a third width greater than the second width; wherein:
   the backing forms a bottom to the inlet port, the injection channel and the post injection reservoir;
   the inlet port is adapted to sequentially move an individual organism into the injection channel, which is adapted by size to immobilize the individual organism in fluid, and,
   the exterior side wall of the injection channel is configured to: i) receive the microinjection pipette without obstruction from any component of the microinjection chip other than the sidewall; ii) be directly penetrable by the microinjection pipette, without a microinjection port; and, iii) reseal upon removal of the microinjection pipette.

2. The microinjection device of claim 1, wherein the injection channel side wall is formed from a material that allows the microinjection pipette to enter and be removed without forming an opening, and without breaking or clogging the microinjection pipette.

3. The microinjection device of claim 2, wherein the injection channel side wall comprises a silicone polymer.

4. The microinjection device of claim 3, wherein the silicone polymer comprises a polydimethylsiloxane (PDMS) elastomer.

5. The microinjection device of claim 1, wherein the inlet port, the injection channel and the post injection reservoir are formed with a polymer material forming a chip comprising the inlet port, the injection channel and the post injection reservoir.

6. The microinjection device of claim 1, further comprising a pre-injection reservoir connected in series to, and in fluid communication with, the inlet port and the injection channel.

7. The microinjection device of claim 1, wherein the unicellular or multicellular organisms are embryos or oocytes.

8. The device of claim 1, wherein the backing comprises glass or plastic.

9. A method for microinjection of a liquid material into a unicellular or multicellular organism, comprising:
   a) adding a fluid comprising the unicellular or multicellular organism to the inlet port that is in fluid communication with an injection channel according to the device of claim 1;
   b) placing the device comprising the unicellular or multicellular organism onto a stage of a microscope that comprises a micromanipulator wherein the microinjection pipette is positioned in a resting position;
   c) injecting liquid material into the unicellular or multicellular organism by moving the microinjection pipette comprising the liquid material through the side wall and penetrating the unicellular or multicellular organism that is stabilized in fluid within the injection channel; and,
   d) moving the microinjection pipette to the resting position and moving the unicellular or multicellular organism to the post injection reservoir.

10. The method of claim 9, further comprising use of a syringe attached to the inlet port to move the unicellular or multicellular organism from the inlet port to the injection channel and into the post injection reservoir.

11. The method of claim 9, further comprising applying pressure to the inlet port to move the unicellular or multicellular organism from the inlet port to the injection channel and into the post injection reservoir.

12. The method of claim 9, wherein the liquid material comprises nucleic acid, chemical compounds or enzymes in an aqueous solution.

13. The method of claim 9, wherein the inlet port, the injection channel and the post injection reservoir are in fluid communication with each other and comprise an osmolarity controlled buffer solution.

14. The method of claim 9, wherein the unicellular or multicellular organism is an embryo or oocyte.

15. The method of claim 9, wherein the multicellular organism is a nematode or fruit fly larva.

16. The method of claim 9, wherein the injected multicellular organisms are removed from the post injection reservoir and selected by sorting fluorescently labeled recovered organisms and/or by selecting recovered non-fragmented organisms.

* * * * *